United States Patent [19]

Carodiskey

[11] Patent Number: 5,699,803
[45] Date of Patent: Dec. 23, 1997

[54] METHOD OF PERFORMING ULTRASONIC EXAMINATION

[75] Inventor: Thomas J. Carodiskey, McVeytown, Pa.

[73] Assignee: Emerson Electric Co., St. Louis, Mo.

[21] Appl. No.: 689,416

[22] Filed: Aug. 9, 1996

[51] Int. Cl.⁶ .................................................. A61B 8/00
[52] U.S. Cl. ................................. 128/660.01; 128/898
[58] Field of Search .................... 128/662.03, 660.01, 128/662.06; 2/51

[56] References Cited

U.S. PATENT DOCUMENTS 5,566,391  10/1996  Williamson ........................ 2/51
5,568,810  10/1996  Hamers et al. ............... 128/660.01

*Primary Examiner*—Marvin M. Lateef
*Assistant Examiner*—Derrick Fields
*Attorney, Agent, or Firm*—Polster, Lieder, Woodruff & Lucchesi

[57] ABSTRACT

A method of performing an ultrasonic examination with a transducer/receiver through a coupling gel including loading the coupling gel in a stand-on-end container which can be maintained in an upside down, standby position without leaking; maintaining the container in a standby position; applying the coupling gel to a subject; performing the ultrasonic examination with the transducer/receiver through the coupling gel; reading the ultrasonic image; and returning the container to the standby position for ready use.

8 Claims, 2 Drawing Sheets

METHOD OF PERFORMING ULTRASONIC EXAMINATION

BACKGROUND OF THE INVENTION

This invention relates generally to the application of a semi-viscous material to a body and, more particularly, to a method of applying transducer couplant prior to attaching the transducer for ultrasonic inspection. While the invention is described in particular detail with respect to medical applications, and in particular to use on a patient's body before connecting an ultrasonic transducer/receiver to the patient, those skilled in the art will recognize the wider applicability of the inventive principles disclosed herein, particularly to industrial applications.

Ultrasonic examination of a patient's internal organs have remarkably improved the physician's ability to diagnose disease or abnormal states and have replaced radiographic imaging in many procedures. For example, ultrasonic examination can be used to diagnose gall bladder disease and visualize the presence of gall stones. Further, the use of ultrasonic examination in obstetrics is well-known. Virtually every obstetrician performs an ultrasonic examination of the developing fetus by performing an "ultrasound" on the pregnant woman.

Basically, in a medical procedure, for example, ultrasonic examination is conducted by applying a transducer to the patient's body while the transducer generates vibrations or sound waves having a frequency above the audible range, with a frequency above 20,000 hertz, directed at the target tissue. Simply stated, the sound waves are produced by the transducer which converts electrical or magnetic energy into the desired vibrations. The sound waves are deflected by the target structure, the fetus for example, and picked up either by the same transducer acting as a receiver, or a separate receiving transducer. The waves can be converted to a useful data including a visual image which can be viewed on a screen. The image often is captured by a form of still photography.

When performing an ultrasonic examination on a patient, best results are obtained when the hand-held probe, including a sending and receiving transducer, makes good contact with the patient's body. To that end, a couplant, commonly a gel, is applied to the patients skin and then the probe is maneuvered through the coupling gel. The couplant or gel commonly is provided in a container, such as a squeeze bottle or tube. The bottle or tube generally is set on a flat surface, such as a cabinet top, near the ultrasound machine and the operator opens the bottle or tube, squeezes on the couplant, and the sets the bottle or tube back on the flat surface. If the bottle or tube has been used, and the level of the gel in the container is low, it is often difficult to get the remaining couplant out of the container. The user must turn the bottle or tube upside down and shake the gel down to the outlet. This is time consuming and inefficient in that it requires technician time and may result in the container being discarded with couplant left inside, since it is so difficult to empty. The technician may try to expedite the process by storing the bottle or tube upside down, but that procedure may result in leaking or loss of couplant due to the outrush of couplant when the outlet is opened. Further, such manipulation of the couplant container can consume valuable time in the event the ultrasonic examination is required in an emergency situation. The ultrasound technician must locate a container of couplant, open it, wait for the couplant to drain toward the outlet, and then apply the couplant. If the user is holding the transducer, this task is generally is carded out with only one hand.

It will be appreciated, however, that ultrasonic inspection has wide application on inanimate objects as well and is employed in the manufacturing and structural arts. In ultrasonic inspection, an ultrasound beam travels through the part. An internal defect, such as a crack, interrupts the beam and reflects back a portion of the ultrasonic energy. The amplitude of the energy reflected and the time required for the return indicates the presence and location of any flaws in the workpiece.

The integrity of products, for example products fabricated from metals, can be tested with ultrasonic techniques. In welding, ultrasonic techniques are utilized to determine the depth of many types of defects in welds and plate material and for gauging the thickness of plate. The technique can be used to test railroad wheels, pressure vessels and die blocks from various directions. Ultrasonic inspection has advantages over other methods since portable equipment can be used and the test can reveal small root cracks and defects not indicated by radiographic film, for example.

Usually in these application, the ultrasonic waves are generated by transducers operating on the principle of piezo electricity. Most inspections are carded out at a frequency range of 1 to 25 MHz. Couplants are used to transmit the ultrasonic waves from the transducer to the test piece. Typical couplants in this application can also include oil, glycerin and grease and are subject to the same problems as stated above relative to medical applications. The present invention is intended for those uses also.

It would be advantageous, therefore, to have a procedure for performing an ultrasonic examination wherein the couplant is readily available and readily applicable, even in an emergency situation. Moreover, it would be advantageous to have such a procedure that allowed for the most efficient and cost-effective use of the couplant.

Those skilled in the art will recognize that the same problems and/or considerations exist in all applications of ultrasonic technology.

SUMMARY OF THE INVENTION

It is among the primary objects of the present invention to provide a method of performing an ultrasonic examination wherein the couplant is readily applied for the procedure.

Another object of the present invention is to provide a method of performing an ultrasonic examination wherein the couplant is provided in a container that allows the ready application of the couplant.

Still another object of the invention is to provide a method of performing an ultrasonic examination wherein the couplant does not leak or waste.

Another object of the invention is to provide a method of performing an ultrasonic examination wherein the couplant is conveniently stored on the user's person to provide immediate access to the couplant.

A further object of the invention is to provide a method of performing an ultrasonic examination wherein the couplant can be stored upside down without leaking or waste.

A still further object of the invention is to provide a method of performing an ultrasonic examination wherein the couplant is provided in a container that can be hung upside down from the user's belt or the like to provide immediate and ready access to the couplant in the container.

These and other objects of the invention will be apparent from the following specification and the accompanying drawings.

In accordance with the invention, a method of performing an ultrasonic examination is provided wherein transducer couplant is loaded into a stand-on-end dispensing container. The container has an outlet configuration that allows for the desired dispensing of the couplant but does not allow leakage even if the outlet is left opened or uncovered. The container is stored, standing on end in a stand-by position so that the viscous yet flowable couplant is readily available at the outlet of the container. The container can have a hanger element on the opposite end so that the container can be suspended or hung from the belt of a user or other convenient location. The container is readily grasped by the user and opened, if necessary. However, the container can be left open, even when the container is inverted. The couplant is applied prior to the test so that an ultrasonic transducer makes good contact. Next, the ultrasonic transducer is applied to at the couplant. The ultrasonic data is transmitted to an appropriate reading device and then read. The couplant container then is replaced in a standby position.

BRIEF DESCRIPTION OF THE DRAWINGS

Corresponding reference numeral indicate corresponding structure throughout the various drawings.

DESCRIPTION OF THE PREFERRED EMBODIMENT

Figure 1:
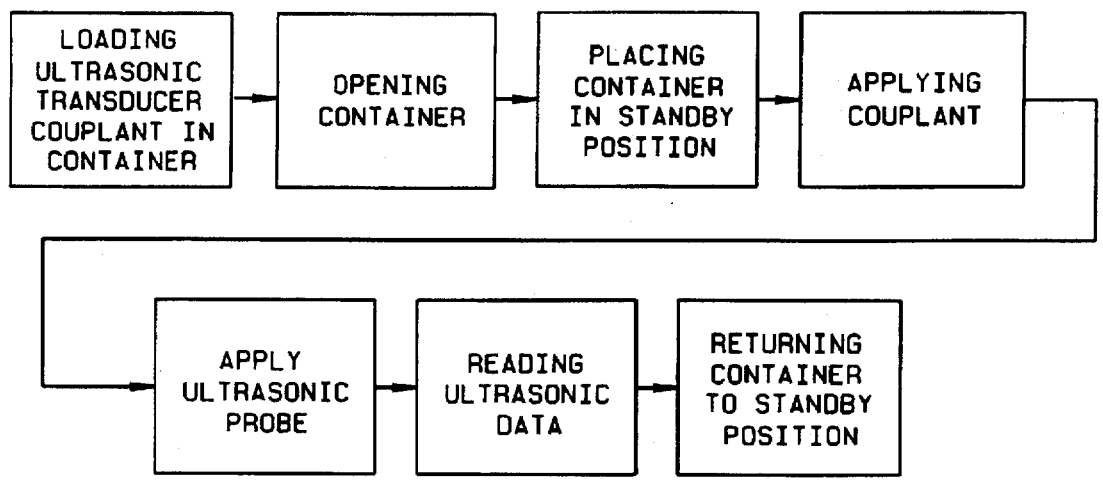
FIG. 1 is a block diagram of the method of performing an ultrasonic examination of the present invention.

The method of performing an ultrasonic examination of the present invention is best illustrated by FIG. 1. The method of the present invention begins by the loading of an ultrasonic coupling gel or couplant in a container. The couplant generally is gel that is viscous, yet flowable. In general, the gel is a conventional transducer gel which is non-toxic, nonflammable, and water soluble. The couplant is loaded in a container 10 best illustrated in FIG. 4, as will now be described in greater detail.

Figures 4, 5:
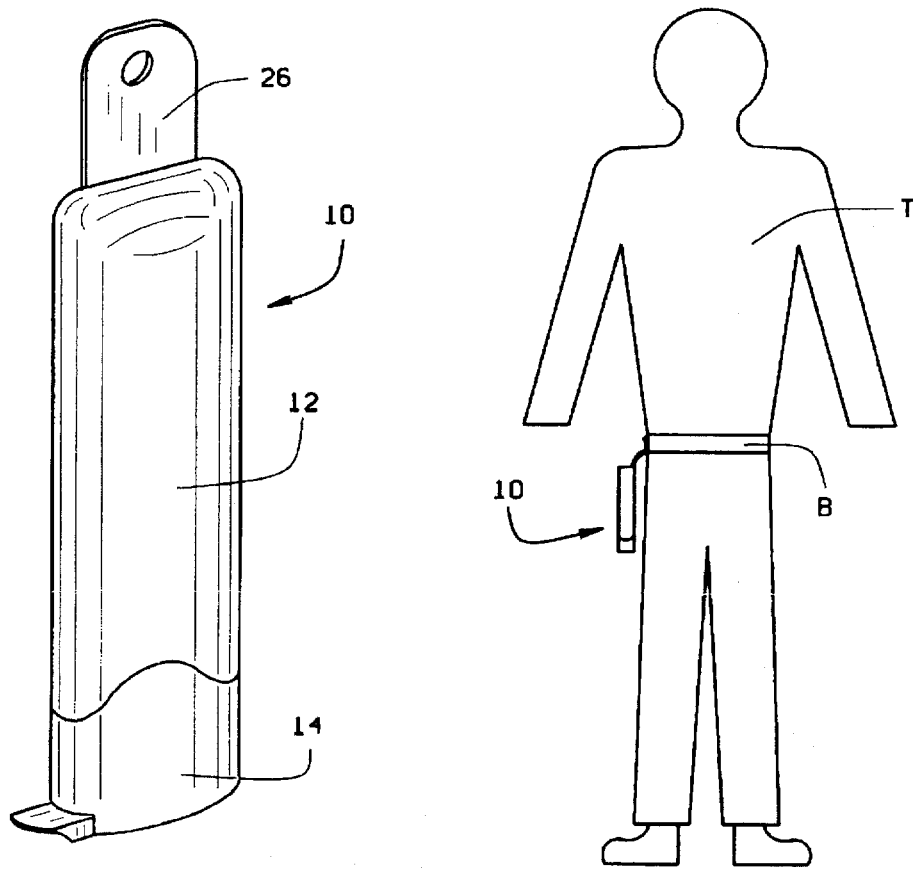
FIG. 4 is an isometric view of a couplant container used in the methods of the present invention, in a standby position.
FIG. 5 is a perspective view of a technician with the couplant container of FIG. 4 suspended from a belt in a standby position.
Figure 2:
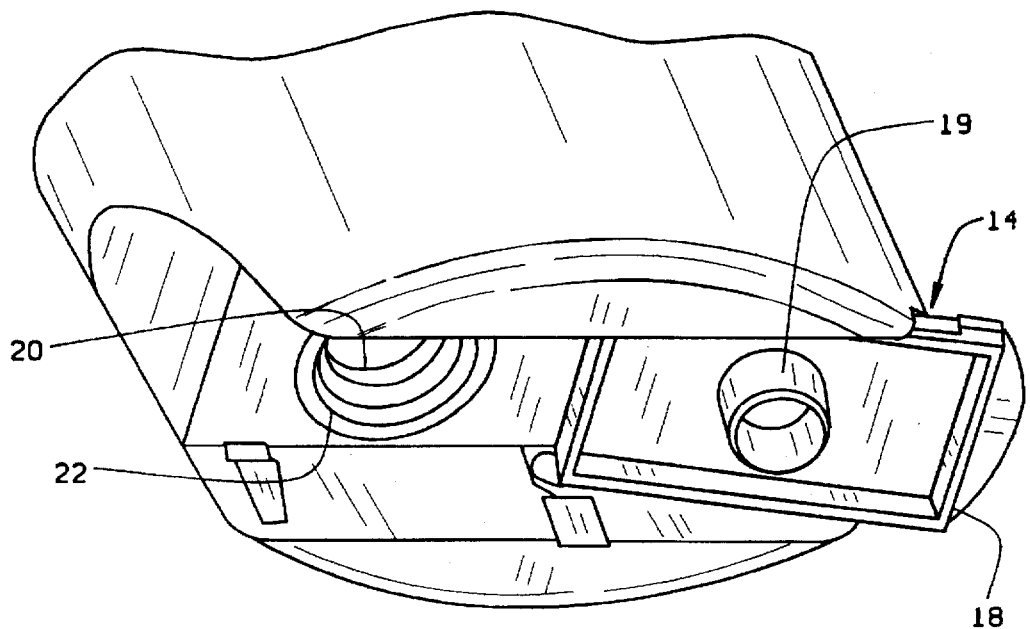
FIG. 2 is a top plan of a prior art container closure used with the methods as illustrated in FIG. 1.
Figure 3:
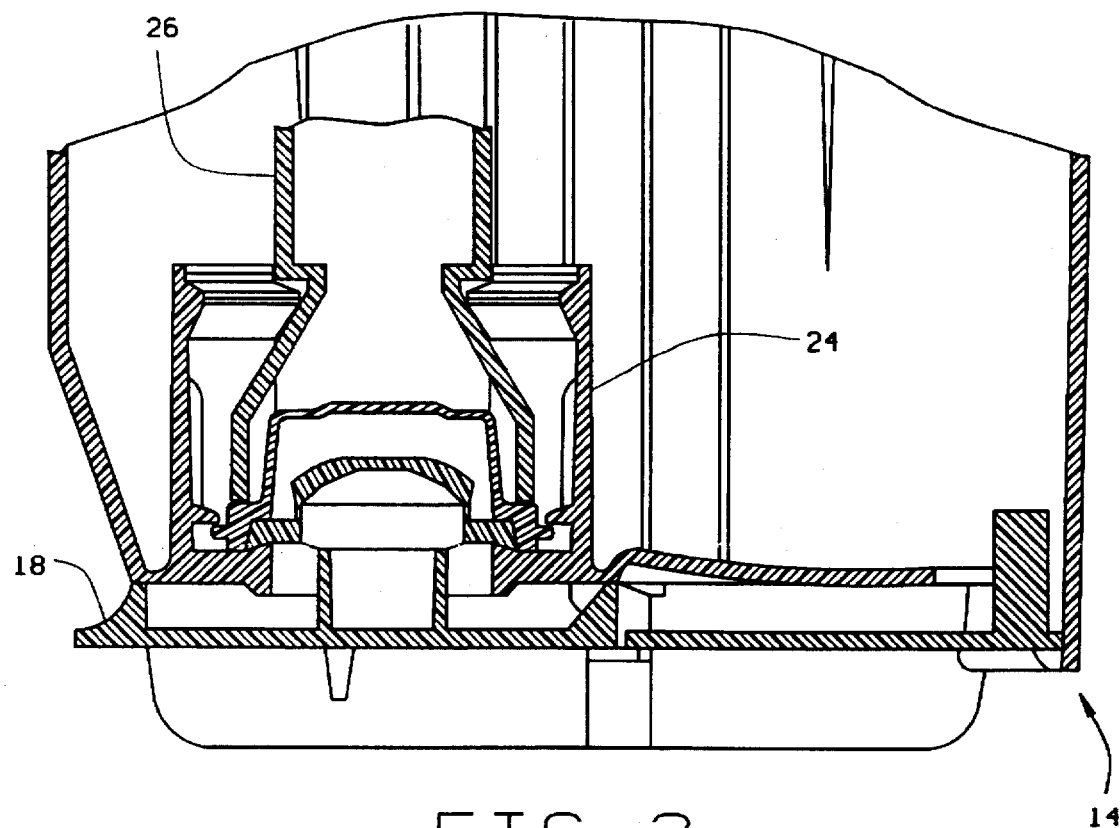
FIG. 3 is a cross-sectional view of the prior art closure of FIG. 2.

Container 10 is a squeezable container having a generally ovoid tubular container body 12 and a dispensing cap 14. The oval design allows the container to better fit in a user's pocket, if desired, for example. Dispensing cap 14, as illustrated in FIGS. 2, 3 and 4 is a prior art dispensing cap available from Seaquist Closures, 711 Fox Street, Mukwonago, Wis. 53149. Dispensing cap 14 includes a snap-open, hinged lid 18 which can be moved from a closed to an open position. Lid 18 includes a plug 19. Further, cap 14 includes a silicone dispensing valve 20 within a housing cartridge 22, as seen in FIG. 2. The silicone dispensing valve 20 seat within neck ring 24. The neck ring 24 snaps over a outlet neck 26 formed on the outlet end of the body. When lid 18 is closed, plug 19 seats in housing cartridge 22. However, the lid is not needed to prevent outflow of gel. The silicone dispensing valve 20 prevents the outflow of gel unless a greater enough squeezing pressure is applied to body 12 to open valve 20 and allow the outflow of the gel. That is, container 10 can be stored upside-down, with lid 18 open and gel will not flow out of the valve, unless the container is squeezed. For example, it can be stored upside-down and open in a user's pocket. Thus, the container can be referred to as a "stand-on-end" container. Moreover, since the container cannot leak, it can remain open and allow easy one-handed use, particularly if the user is holding a transducer in one hand.

Container 10 preferably also includes a loop 26 or other attachment means for attaching the container 10 to the belt B of a user or ultrasound technician T, as shown in FIG. 5. Since the container 10 does not leak, even when placed in a standby or upside-down position, the container can be suspended from the belt of a user in an open position, thereby making the couplant readily available. It will be appreciated that although container 10 is illustrated having a loop 26 for upside-down suspension, any type of appropriate structure for releasably suspending the container in a standby or "stand-on-end" position is contemplated by the invention. For example, the container could be inverted in a holster or the like. Other forms of loops, such as Velcro® or the like, can be used, if desired.

After the couplant is loaded in the container, the container 10 can be opened or container 10 can be stored or placed in a "standby" position, upside-down or vice versa. As stated above, the container cannot leak couplant material. Thus, the container can be placed or stored upside down, meeting several objects of the present invention. First, since the coupling gel is semi-viscous, it does not flow readily. By placing container 10 in a standby position, the gel can slowly flow to the dispensing orifice or valve 20. Hence, it ready for application. By contrast, if the container is stored with the dispensing end up, the user must shake and squeeze and force the gel toward a dispensing or outflow orifice. This is time consuming, particularly as the volume of coupling gel decreases in the container. Often, a container would be discarded with gel inside because it is difficult to dispense the remnants. Moreover, having the couplant readily dispensable is advantageous in emergency situations.

As seen in FIG. 5, and as explained above, container 10 can be suspended from the user's belt in a standby position.

Next, the couplant is applied to the patient's body, over the target site, in a conventional manner. The ultrasonic probe or transducer/receiver then is applied, also in a conventional manner. A conventional hand-held, directly coupled probe may be used. However all types of ultrasonic examination procedures are contemplated by the method of the invention. The data is transmitted to a reading device and read by the technician or physician. Finally, container 10 is returned to a standby position, ready for the next application.

It will be appreciated that various changes and modifications may be made in the method of the present invention without departing from the scope of the appended claims. For example, several of the steps illustrated in FIG. 1 can be taken out of sequence, without departing from the invention. Moreover, a number of standby positions are contemplated. For example, the container may be suspended from an extendible lanyard, a wall hook, a lanyard or elastic cord or even a conventional i.v. pole or the like. While a particular container valve is described in the preferred embodiment, other container valve constructions are compatible with the broader aspects of the invention. Therefore, the foregoing description and accompanying drawings are intended to be illustrative only and should not be viewed in a limiting sense.

I claim:

1. A method of applying couplant required for an ultrasonic transducer reading comprising the steps of:

loading ultrasonic transducer couplant in a container having at least a first open end for dispensing the couplant and a structure for closing the open end;

opening the structure closing the first end of the container so couplant is ready to apply;

placing the open end of the container in a vertical standby position, open end down, so that couplant feeds towards the open end and is ready for use;

applying couplant to a test subject having an ultrasonic test;

applying an ultrasonic transducer at the couplant;

reading ultrasonic data produced by said transducer through the couplant;

returning the container to the standby position; and preventing couplant flow from the container in the standby position through said structure.

2. The method of claim 1 wherein couplant is provided for hand-held directly coupled ultrasonic examination.

3. The method of claim 1 wherein the container further includes a fastening device for releasably fastening the container to a user so that the container is suspended in the standby position when not applying couplant.

4. A method of performing an ultrasonic examination on a subject with an ultrasonic transducer/receiver comprising the steps of:

placing a container of couplant in a standby position wherein the container is placed with a dispensing orifice faced vertically downwardly so that couplant feeds towards the dispensing orifice to facilitate evacuation of the couplant from the container, the container including a valve mechanism to prevent unwanted outflow of the couplant while the couplant is in the standby position;

applying the couplant to the subject;

applying the ultrasonic transducer/receiver to the couplant;

obtaining ultrasonic data through the transducer/receiver; and reading the ultrasonic data.

5. The method of claim 4 wherein the standby position further includes suspending the container in it's standby position when not being used for couplant application.

6. The method of claim 5 wherein the container is suspended from the body of a user.

7. A container for the ready application of a transducer coupling gel comprising:

a hollow body for the loading of coupling gel, said body having a first end and a second end, said first end having an outflow orifice formed therein;

a dispensing cap at said first end and fluid connection with said outflow orifice, said dispensing cap having a valve mechanism therein for preventing the unwanted flow of the coupling gel through the dispensing cap, said dispensing cap having at least one flat area for supporting said container in a standby, cap downward position enabling couplant to feed towards said cap; and a suspending loop along said second end for releasably suspending the container in it's standby position so that couplant is immediately available for use upon activation of said valve.

8. The container of claim 7 wherein said one flat surface area supports said container on a surface in its downward position.

* * * * *